United States Patent [19]
Haug

[11] Patent Number: 5,659,984
[45] Date of Patent: Aug. 26, 1997

[54] SNOW GROOMING DEVICE

[75] Inventor: Walter Haug, Blaustein, Germany

[73] Assignee: Kässohrer Geländefahzeug GmbH, Germany

[21] Appl. No.: 381,929

[22] PCT Filed: Dec. 2, 1993

[86] PCT No.: PCT/EP93/03396

§ 371 Date: Feb. 14, 1995

§ 102(e) Date: Feb. 14, 1995

[87] PCT Pub. No.: WO94/15028

PCT Pub. Date: Jul. 7, 1994

[30] Foreign Application Priority Data

Dec. 21, 1992 [DE] Germany ............... 9217472 U

[51] Int. Cl.$^6$ ............... A63C 19/10; E01H 4/00
[52] U.S. Cl. ............... 37/219; 37/223; 172/123; 172/684.5
[58] Field of Search ............... 37/219, 220, 221, 37/222, 223, 224; 172/118, 122, 123, 112, 654, 684.8

[56] References Cited

U.S. PATENT DOCUMENTS

| | | | |
|---|---|---|---|
| 2,911,734 | 11/1959 | Sublett et al. | 37/104 |
| 3,652,106 | 3/1972 | Waterman | 37/223 X |
| 3,746,101 | 7/1973 | Takata | 172/112 |
| 4,051,902 | 10/1977 | Van Der Lely | 172/123 X |
| 4,142,587 | 3/1979 | Woodwar et al. | 172/123 X |
| 4,163,329 | 8/1979 | Neff | 37/222 |
| 4,348,825 | 9/1982 | Bächler | 37/222 |
| 4,359,831 | 11/1982 | Beeley | 172/112 X |
| 4,523,398 | 6/1985 | Scheibel et al. | 37/219 |
| 4,726,129 | 2/1988 | Haug | 37/222 |
| 4,775,017 | 10/1988 | Ranner | 37/222 X |
| 4,788,783 | 12/1988 | Bachler | 37/220 |
| 5,067,263 | 11/1991 | Pelletier | 37/219 X |

FOREIGN PATENT DOCUMENTS

| | | | |
|---|---|---|---|
| 3025312 | 2/1981 | Germany . | |
| 2946796 | 5/1981 | Germany | 37/219 |
| 3417758 | 11/1985 | Germany | 37/219 |
| 9212233 | 11/1992 | Germany . | |
| WO81/03353 | 11/1981 | WIPO . | |

*Primary Examiner*—Terry Lee Melius
*Assistant Examiner*—Thomas A. Beach
*Attorney, Agent, or Firm*—Samuels, Gauthier, Stevens & Reppert

[57] ABSTRACT

A snow grooming devise is provided with a carrier frame consisting of at least one transverse supporting member and two longitudinal supporting members so that it is adapted to be attached to a vehicle with the aid of a coupling means. A vertically adjustable snow propeller and a smoothing board are mounted on the carrier frame. The carrier frame is mounted on said coupling means such that it is adapted to be pivoted about an essentially horizontal longitudinal axis and an essentially horizontal transverse axis. The snow propeller is dragged by the front ends of the longitudinal supporting members and is pivotably mounted thereon and the transverse supporting member is associated with the coupling means so as to support the carrier frame.

34 Claims, 3 Drawing Sheets

SNOW GROOMING DEVICE

BACKGROUND OF THE INVENTION

1. Field of the Invention

The present invention refers to a snow grooming device adapted to be attached to a vehicle with the aid of a coupling means, comprising a carrier frame, which consists of at least one transverse supporting member and two longitudinal supporting members and on which a vertically adjustable snow propeller and a smoothing board are mounted, said carrier frame being mounted on said coupling means such that it is adapted to be pivoted about an essentially horizontal longitudinal shaft and an essentially horizontal transverse shaft.

2. Description of the Prior Art

Such a snow grooming device is known from DE-A-29 46 796. In this reference, the snow grooming device is coupled to the tail of a vehicle via a drag bar. At the rear end of the drag bar, a carrier frame is supported by means of two longitudinal supporting member ends such that it is adapted to be pivoted about a horizontal transverse shaft and a horizontal longitudinal shaft. When seen in a side view, the carrier frame has an essentially V-shaped structural design, a smoothing board and, adjacent thereto, a snow propeller being pivotably supported at the rear end of said carrier frame. With the aid of two adjusting means, the snow propeller is vertically adjustable and an angle of inclination of the smoothing board can be varied, said two adjusting means being provided between the carrier frame and the snow propeller and the carrier frame and the smoothing board, respectively. The smoothing board is followed by a finisher.

The snow grooming device known from DE-A-29 46 796 is disadvantageous insofar as its overall length, which is necessary for pivotably raising the snow grooming device to a ready position, is comparatively large. This restricts the manoeuverability of the vehicle; in particular, cornering is only possible with a comparatively large radius. Hence, it will be difficult to groom the snow on pistes by directly adjoining passages of the snow grooming device. Due to the fact that the snow propeller is arranged such that it is "pushed", steering of the snow grooming device is additionally made more difficult in a disadvantageous manner, since the tracking properties of the snow grooming device are disadvantageous due to the pushed mode of arrangement. Another drawback is that the carrier frame is arranged such that it defines a U which is open in the direction of the vehicle, whereby the rigidity of the carrier frame is influenced unfavourably.

SUMMARY OF THE INVENTION

Hence, it is the object of the present invention to improve a snow grooming device of the type mentioned at the beginning with respect to its manoeuverability and ease of operation as well as with respect to its compact structural design while simultaneously increasing the rigidity thereof.

In connection with a snow grooming device having the features of the generic clause of claim 1, this object is achieved by the features that the snow propeller is dragged by the front ends of the longitudinal supporting members and is pivotably mounted thereon and that the transverse supporting member, which is used for supporting the carrier frame, is associated with the coupling means.

Due to the fact that the snow propeller is arranged on a tail or front side of a vehicle such that it is dragged, the manoeuverability and ease of operation of the snow grooming device as a whole is improved. With the aid of the coupling means, the carrier frame is adapted to be pivoted directly, without any drag bar, into a ready position and back into a position of use. The overall length of the snow grooming device is thus substantially reduced. This has the effect that also the curve radius occurring when the snow grooming device turns a corner is reduced so that the groomed sections of the piste will be arranged directly side by side or, if desired, also such that they will partially overlap one another, without any manoeuvering of the vehicle, which has attached thereto the snow grooming device, being necessary. Due to the fact that the transverse supporting member is associated with the coupling means, the carrier frame of the snow grooming device is reinforced in an advantageous manner especially at the point of application of the force applied by the vehicle. The force is introduced in the transverse supporting member so that, in comparison with the introduction of the force into the spaced longitudinal supporting members, which is described in DE-A-29 46 796, the coupling means has a smaller width and a less complicated structural design. In view of the fact that the snow propeller is articulated on the front ends of the longitudinal supporting members, the distribution of weight in the carrier frame is improved insofar as the weight arms acting on the essentially horizontal transverse shaft of the coupling means are comparatively short so that the snow grooming device can more easily be pivoted to its ready position.

In accordance with one further development of the present invention, the transverse supporting member extends between the longitudinal supporting members and is, essentially at the centre thereof, pivotably mounted on said coupling means. The carrier frame is thus reinforced in a simple manner, and, by means of the transverse supporting member, it is mounted such that it can easily be pivoted between a ready position and a position of use.

Another advantageous feature is that, when seen in a side view, the longitudinal supporting members are essentially U-shaped, each of said longitudinal supporting members comprising a U-crosspiece and a front and a rear U-leg. The snow propeller and the smoothing board can thus be arranged at the ends of the U-legs in a simple manner, the smoothing board being arranged subsequent to the snow propeller. The snow propeller can be adjusted vertically in accordance with the length of the U-legs, said snow propeller being adapted to be raised until it is located adjacent the U-crosspiece. A maximum lifting height can, for example, be 250 mm in the case of one embodiment of the invention.

In accordance with another embodiment of the present invention, the front U-leg associated with the snow propeller defines essentially a right angle with the U-crosspiece and the rear U-leg associated with the smoothing board defines an obtuse angle with said U-crosspiece. The carrier frame can thus be mounted on the coupling means directly adjacent the front U-leg so that the area through which said carrier frame moves when it is pivoted between the ready position and the position of use is comparatively small. The smoothing board is, at the same time, arranged at a sufficient distance from the snow propeller.

In order to mount the snow propeller such that it can easily be pivoted relative to the carrier frame, a bearing sleeve is arranged on the free end of the front U-leg, said bearing sleeve being used for receiving therein a bearing bolt which is adapted to be rotated about an essentially horizontal longitudinal axis and at the rear end of which the snow propeller is mounted such that it is adapted to be pivoted about an essentially horizontal transverse axis. The snow propeller will thus be able to follow uneven areas of the piste at least partially.

The snow propeller comprises, by way of example, a propeller frame and a propeller shaft rotatably mounted on said propeller frame, said propeller frame being articulated on the front U-legs. The propeller frame is, in a simple manner, used for mounting the propeller shaft as well as for articulation on the carrier frame.

For additionally reducing in size snow and/or broken pieces of frozen snow or ice thrown up by the blades arranged on the propeller shaft and for achieving a low discharge of snow towards the front as well as for preventing snow from being thrown over the snow propeller, the propeller frame comprises an essentially semicircular baffle casing at the lateral ends of which the propeller shaft is rotatably supported as well as two longitudinal control arms arranged between the U-leg ends and said baffle casing. By means of these longitudinal control arms, the distance from the propeller shaft to the front ends of the U legs is determined such that the snow propeller as a whole can be pivoted in the best possible way.

For simplifying the vertical adjustment of the snow propeller, at least one adjusting means is arranged between the longitudinal control arm and the U-crosspiece. The adjusting means is adapted to be used for adjusting the snow cutting depth as well as for improving, in the condition in which the snow grooming device is attached to the vehicle, the hill climbing properties of the vehicle by means of the contact pressure applied by the snow propeller. The snow propeller can, for example, be raised in the direction of the carrier frame until the baffle casing abuts on the U-crosspiece from below.

In order to facilitate the arrangement of the adjusting means, it will be advantageous when the front U-leg is connected to the U-crosspiece via a connecting portion bent outwards at an acute angle. The adjusting means can thus be arranged parallel to the direction of adjustment of the snow propeller, an upper end of said adjusting means being, by way of example, pivotably supported on the side of the U-crosspiece. This permits easy access to the adjusting means so that respective connections for actuating the adjusting means can easily be established and so that said adjusting means can also be serviced without any difficulties.

In order to further facilitate the manoeuverability and ease of operation of the snow grooming device, it will be particularly advantageous when the transverse supporting member is arranged adjacent to the connecting portions of the front U-legs between the U-crosspieces and is supported on the coupling means such that it is adapted to be pivoted about the essentially horizontal transverse axis.

In this connection, it will also be advantageous when the transverse supporting member is mounted on the coupling means via two bearing brackets extending approximately in the direction of the free end of the front U-leg. The horizontal transverse axis can be arranged behind the horizontal longitudinal axis, when seen in the longitudinal direction of the snow grooming device, as well as below the horizontal longitudinal axis in the case of another embodiment. The bearing brackets can be attached e.g. at two ends of a bearing bolt which is rotatably supported in the coupling means.

It will be advantageous when the coupling means has arranged thereon a stop means for the transverse supporting member so that the carrier frame provided in the case of a simple embodiment will be urged in the direction of the piste surface when the coupling means is pivoted by the vehicle.

In the case of an advantageous embodiment of the baffle casing of the propeller shaft, said baffle casing consists of a hollow section with reinforcement tubes extending within said hollow section essentially parallel to the propeller shaft, said baffle casing being covered at the sides by aprons extending essentially at right angles to said propeller shaft. These aprons are simultaneously used for supporting the propeller shaft. Due to the hollow section and the reinforcement tubes, the baffle casing has a stable structural design and a low weight. The lateral aprons prevent edge wall formation by heaped up snow or the like.

The baffle casing can, for example, be made from plastic material or also from metal sheets. In addition, the lower surface of the baffle casing associated with the propeller shaft can be made from a material which differs from the material which has been used for the upper surface facing outwards.

In order to increase the flexibility of the snow propeller, said snow propeller consists, in accordance with an advantageous embodiment, of two propeller shafts with adequate propeller frames, the longitudinal control arms of each propeller frame being arranged essentially centrally on the respective frame when seen in the transverse direction. The two propeller shafts can especially have a uniform structural design so that the production costs will be reduced. Due to the fact that the individual propeller frames and the propeller shafts belonging thereto are supported separately via the longitudinal control arms associated therewith, the snow propeller can be adapted to uneven areas of the piste. Especially the marginal areas of the piste can thus be groomed more easily, and, due to the fact that the piste is not levelled completely in the direction of the propeller shafts, it will be possible to provide an interesting skiing course for a skier instead of a "dull" flat piste. A divided propeller shaft is known e.g. from "Logan Manufacturing's Contour Grooming/Flex Tiller" (1990), but the propeller shaft of this snow grooming device consists of three propeller shafts which are articulated on one another. Due to the two articulation points, the efficiency of the snow propeller is reduced and a separate adjustment of each propeller shaft is not possible.

In this connection, it will be particularly advantageous when each propeller shaft has associated therewith a drive means. With the aid of these drive means, the speeds of the propeller shafts can be controlled independently from one another e.g. in the range of from 700 to 1400 rpm. The drive means can be constructed as electric motors, hydrostatic drives or the like, and they can drive directly one end of the respective propeller shaft.

In this connection, it will also be advantageous when the drive means are arranged on outer, lateral ends of the propeller shafts. On the basis of this arrangement, the smallest possible central distance between the propeller shafts, e.g. in the order of 100 mm, can be realized. Due to the fact that each propeller shaft is supported separately, an articulated joint is not required between the two propeller shafts, and, due to the separate drive means, a driving connection between said propeller shafts can be dispensed with as well. This will have the effect that, on the basis of its simple structural design, the whole snow grooming device can be serviced more easily and the production costs will be reduced.

The swivel angles of each propeller shaft in the vertical direction can, for example, be ±10° or larger than that.

For actively resetting the propeller shafts to their colinear arrangement when the vehicle is driving along a flat piste, it will be advantageous when a resetting device is arranged between the propeller frames. In a simple embodiment, the resetting device is arranged between the neighbouring ends of the propeller frames.

In accordance with one embodiment of the resetting device, said resetting device is an elastic flat connector which extends between two reinforcement tubes of the baffle casings in the longitudinal direction and essentially parallel to the longitudinal axis of the longitudinal control arm in its transverse direction. The flat connector can, for example, be made from flat steel or from a material having similar properties. It extends over the gap between the two neighbouring propeller shafts from one reinforcement tube up to and into the other.

In view of the fact that the flat connector is orientated such that its transverse direction extends essentially parallel to the longitudinal axis of the longitudinal control arm, it will apply restoring forces to the propeller shafts especially when non-uniform pivotal movements about the horizontal longitudinal axes of the respective bearing sleeves take place.

It will be advantageous when an axis of rotation of the propeller shaft is arranged below the longitudinal control arm at a distance therefrom so that the propeller shaft can more easily be guided by a swivel bearing.

In order to reinforce the carrier frame at the rear end thereof, it will advantageous when a reinforcement member is arranged adjacent to the free ends of the rear U-legs between said U-legs, said reinforcement member extending essentially parallel to the transverse supporting member.

For releasably fastening and supporting the smoothing board, it will be particularly advantageous when transversely extending smoothing board strips are pivotably supported on the free end of the rear U-leg. These smoothing board strips extend essentially parallel to the propeller shafts and rest on an upper surface of the smoothing board. They can, in the manner known, be supported such that they are adapted to be pivoted about an essentially horizontal longitudinal axis and/or an essentially horizontal transverse axis.

The smoothing board strips can also be constructed such that they will abut on the smoothing board and press said smoothing board onto the underlying piste only if the snow grooming device is at its position of use. In this case, it will be advantageous when at least one smoothing board carrier member protrudes towards the front from the respective smoothing board strips, the free end of said smoothing board carrier member being releasably secured to the smoothing board.

In the case of one embodiment of the smoothing board, said smoothing board consists of a smoothing blade, a guard and a carrier body, the smoothing board carrier members being releasably secured to the carrier body and the guard protruding from said carrier body essentially upwards, whereas the smoothing blade protrudes therefrom essentially downwards. In this case, the smoothing board strip will rest on the surface of the smoothing blade when the snow grooming device is arranged at its position of use.

In this connection, it will also be adavantageous when the smoothing blade and the guard are releasably secured to the carrier body. A simple connection between the carrier body and the smoothing blade and the guard, respectively, can, for example, be established via a dovetaillike connection. The guard and the carrier body can be made e.g. from plastic material or from an adequate metal, the smoothing blade consisting of a flexibel material. The surfaces of the smoothing blade, the guard and the carrier body are in alignment with one another and merge with one another according to an advantageous embodiment.

In this connection, it will also be adavantageous when, complementary to the snow propeller having two propeller shafts, at least the guard is divided in the transverse direction. Due to the fact that the guard is divided into two parts, an adaptation of the smoothing board to uneven areas of the piste will be possible, complementary to the adaptation of the propeller shafts, if, for example, the carrier body is elastic.

For improving the manoeuverability and ease of operation of the snow grooming device, it will also be advantageous when the snow grooming device as a whole is constructed symmetrically with respect to the centre line extending in the longitudinal direction.

In accordance with another embodiment of the present invention, the transverse supporting member extends essentially between the front ends of the longitudinal supporting members and is pivotably mounted on the horizontal transverse shaft via bearing brackets protruding in the direction of the coupling means. In this case, the longitudinal supporting members are e.g. L-shaped, the transverse supporting member and the snow propeller being arranged on the free end of the longer L-leg and the smoothing board being arranged on the free end of the shorter L-leg.

In order to urge the carrier frame in the direction of the piste surface when the snow grooming device is in its position of use, it will be advantageous when a stop lever protrudes from the transverse supporting member essentially upwards, said stop lever being adapted to be brought into abutting contact with at least one abutting arm arranged at the side of the coupling means.

If the snow propeller is constructed such that it includes two propeller shafts, it will be advantageous when the resetting means is constructed as an elastic connector which extends laterally with respect to a reinforcement tube of the propeller frames and which is connected to said propeller frames. As has already been mentioned hereinbefore, the flat connector extends vertically with respect to the swivel plane of the propeller shafts when seen in the transverse direction. This will have the effect that, when the propeller shafts are pivoted relative to one another, i.e. in the case of different rotations of the longitudinal control arms about the horizontal longitudinal axes, the flat connector will be bent in the direction opposite to a restoring force due to its flexibility.

In accordance with an additional embodiment of the present invention, stop arms protrude backwards from the reinforcement transverse supporting member so that abutting levers protruding from the smoothing board can abut thereon. The adjustment angle of the smoothing board in direction of the snow propeller will thus be determined.

In this connection, it will also be advantageous when an adjustment means is arranged between the free end of the stop arm and the smoothing board. This adjustment means can especially be used for applying a force to the smoothing blade of the smoothing board in the direction of the piste surface. In addition, the smoothing board can be raised from the piste surface.

For fastening the adjustment means to the smoothing board in a simple manner, it will be advantageous when at least one bearing bracket is formed on the upper surface of the smoothing board.

BRIEF DESCRIPTION OF THE INVENTION

In the following, advantageous embodiments of the present invention will be explained and described in detail on the basis of the figures shown in the drawing, in which FIG. 1 shows a top view of an embodiment of the snow grooming device according to the present invention;

DESCRIPTION OF THE PREFERRED EMBODIMENTS

Figure 1:
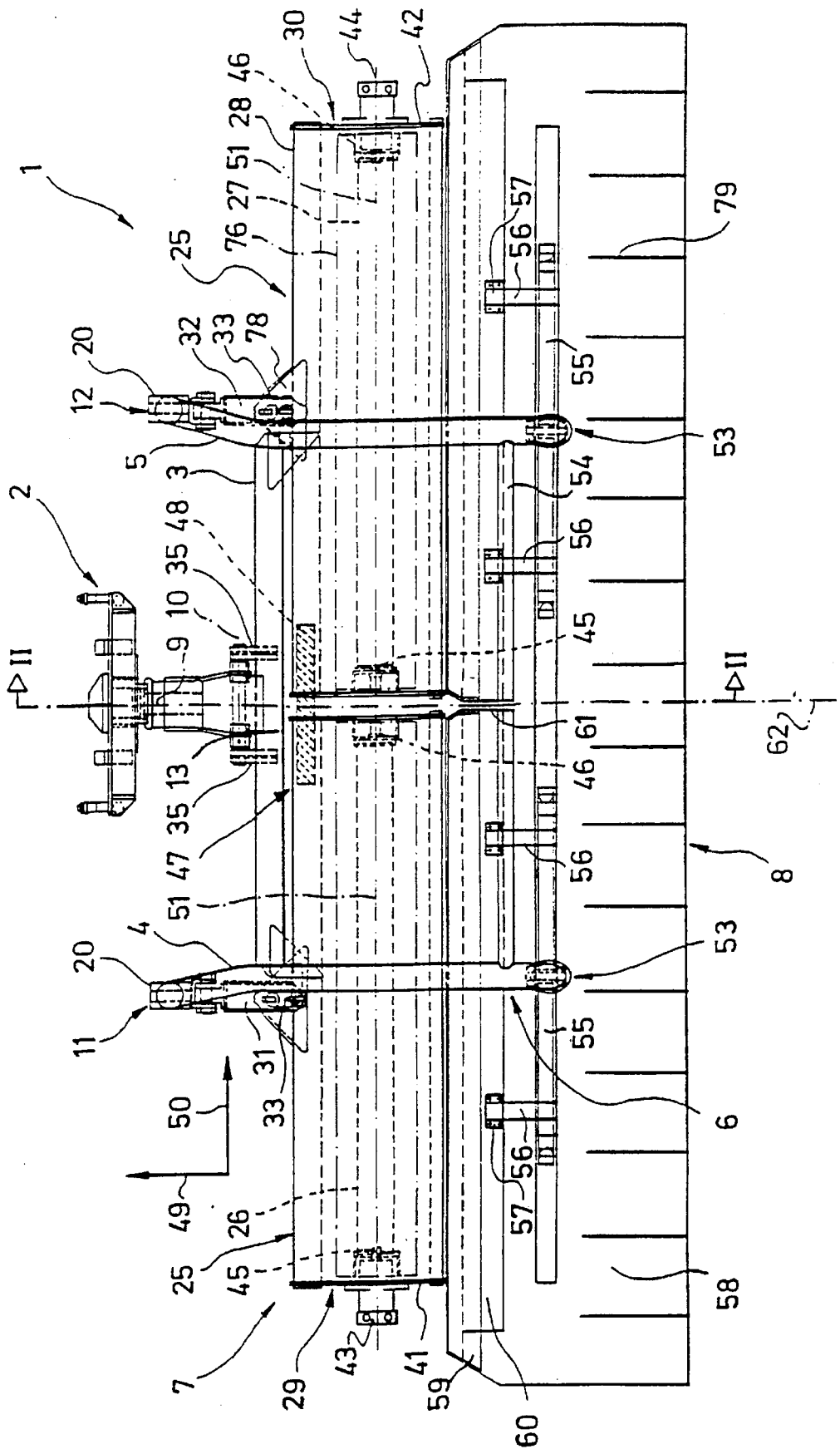

FIG. 1 shows a top view of a snow grooming device 1 comprising a coupling means 2, a snow propeller 7 and a smoothing board 8 following said snow propeller 7. The coupling means 2 serves to couple the snow grooming device 1 to a vehicle which is not shown. Said coupling means 2 is known per se and will be described only in part hereinbelow. Via adequate means provided on the vehicle, said coupling means 2 is adjustably supported on said vehicle in the manner known so that the snow grooming device 1 can be pivoted from a ready position to a position of use and vice versa. In the rear end of the coupling means 2 an essentially horizontal longitudinal axis 9 and an essentially horizontal transverse axis 10 are defined, which serve to pivot the snow propeller 7 and the smoothing board 8.

A carrier frame 6 is provided for supporting the snow propeller 7 and the smoothing board 8, said carrier frame 6 extending essentially above the snow propeller and the smoothing board. The carrier frame 6 comprises a transverse supporting member 3, two longitudinal supporting members 4 and 5 and one reinforcement member 54. The transverse supporting member 3 and the reinforcement member 54 are arranged parallel to one another and extend in the transverse direction 50 of the snow grooming device 1. By means of two spaced bearing brackets 35, the transverse supporting member 3 is, at the centre 13 thereof, mounted on the coupling means 2 such that it is adapted to be pivoted about the essentially horizontal transverse axis 10. The transverse supporting member 3 has a tubular structural design and ends on the sides of the longitudinal supporting members 4 and 5 which face each other, said transverse supporting member 3 being secured to said longitudinal supporting members 4 and 5 at this point.

The longitudinal supporting members 4 and 5 extend essentially at right angles to the transverse supporting member 3 and the reinforcement member 54; in the longitudinal direction 49 of the snow grooming device 1, said longitudinal supporting members 4 and 5 extend beyond the transverse supporting member 3 and the reinforcement member 54 in the direction of the coupling means 2 as well as in the direction towards the smoothing board 8. The ends of the longitudinal supporting members 4 and 5 projecting beyond the transverse supporting member 3 towards the front are bent outwards, i.e. away from the coupling means 2, at an acute angle relative to the longitudinal direction 49. At the free front ends 11 and 12 thereof, bearing sleeves 20 are arranged on which the snow propeller 7 is pivotably supported. The rear ends 53 of the longitudinal supporting members 4 and 5 have pivotably mounted thereon smoothing board strips 55 used for supporting the smoothing board 8.

The snow propeller 7 has a bipartite structural design and comprises a left propeller shaft 26 and a right propeller shaft 27. Both propeller shafts have their lateral ends 45 and 46 rotatably mounted in propeller frames 25. The propeller shafts 26 and 27 are arranged such that their axes of rotation 51 extend parallel to the transverse supporting member 3 or the reinforcement member 54. A plurality of cutting blades protrude from said propeller shafts, said cutting blades extending up to the circumferential line 76 of the propeller shafts 26 and 27. For supporting the propeller frames on the carrier frame 6, longitudinal control arms 31 and 32 project, approximately centrally, from said propeller frames below said longitudinal supporting members 4 and 5 and essentially in parallel therewith. For reinforcing the connection between said longitudinal control arms 31, 32 and a baffle casing 28 surrounding the propeller shafts 26 and 27 at least partially, reinforcement sheets 78 having an approximately triangular shape are arranged between said two members. At the end located opposite the baffle casing 28, the longitudinal control arms 31 and 32 are pivotably supported on the bearing sleeves 20 at the free ends 11 and 12 of the longitudinal supporting members 4 and 5.

The baffle casing 28 is covered by lateral aprons at its outer ends 29 and 30 as well as at the ends which are located adjacent a centre line 62, said aprons being simultaneously used for supporting the propeller shafts 26 and 27. The outer ends 29 and 30 of the baffle casing 28 have arranged thereon drive means 43 and 44 for the propeller shafts 26 and 27, respectively, for separately driving said two propeller shafts. These drive means are arranged essentially concentrically with the axis of rotation 51 of said propeller shafts 26 and 27.

A resetting device 47 is arranged adjacent the transverse supporting member 3 between the two baffle casings 28 of the propeller shafts 26 and 27. Said resetting device consists of a flat connector which extends essentially parallel to the transverse supporting member 3 and part of which is inserted in the baffle casings 28 on both sides of said centre line 62.

Adjusting means 33 for vertically adjusting the propeller shafts 26 and 27, respectively, are arranged between the longitudinal control arms 31 and 32 and the longitudinal supporting members 4 and 5, said adjusting means 33 being provided on the side faces of said longitudinal supporting members 4 and 5 which are located opposite the transverse supporting member 3.

The smoothing board strips 55 associated with the rear ends 53 of the longitudinal supporting members 4 and 5 are, approximately at the centre thereof, mounted on said ends 53 such that they are adapted to be pivoted about an axis extending in the longitudinal direction 49. The smoothing board strips extend symmetrically with respect to the longitudinal supporting members 4 and 5 along the transverse direction 50. Adjacent the ends of said smoothing board strips, smoothing board carrier members 56 project essentially at right angles, the free ends 57 of said smoothing board carrier members 56 being releasably secured to the smoothing board 8.

The smoothing board 8 comprises the carrier body 60 which is releasably connected to the smoothing board carrier members 56, a smoothing blade 58 and a guard 59. Said guard 59 extends in the vicinity of and parallel to the snow propeller 7, and it is interrupted by a central division 61 along the centre line 62. The smoothing blade 58 extends from the carrier body 60 towards the back, the smoothing board strips 55 being releasably secured to the smoothing blade 58 from above. The width of the smoothing board 8 exceeds the width of the snow propeller 7, the drive means 43 and 44 projecting laterally beyond the snow propeller 7 being covered by the lateral ends of said smoothing board 8. The smoothing blade 58 is provided with a plurality of division slots 79, which are arranged parallel to one another and which extend from the rear end of the smoothing blade 58 in the direction of the smoothing board strips 55. The division slots 79 divide the smoothing blade 58 into separate sections in the transverse direction 50, said sections being orientated parallel to the longitudinal direction 49.

The snow grooming device 1 comprising the snow propeller 7 and the smoothing board 8 is constructed such that it is symmetrical with respect to the centre line 62.

Figure 2:
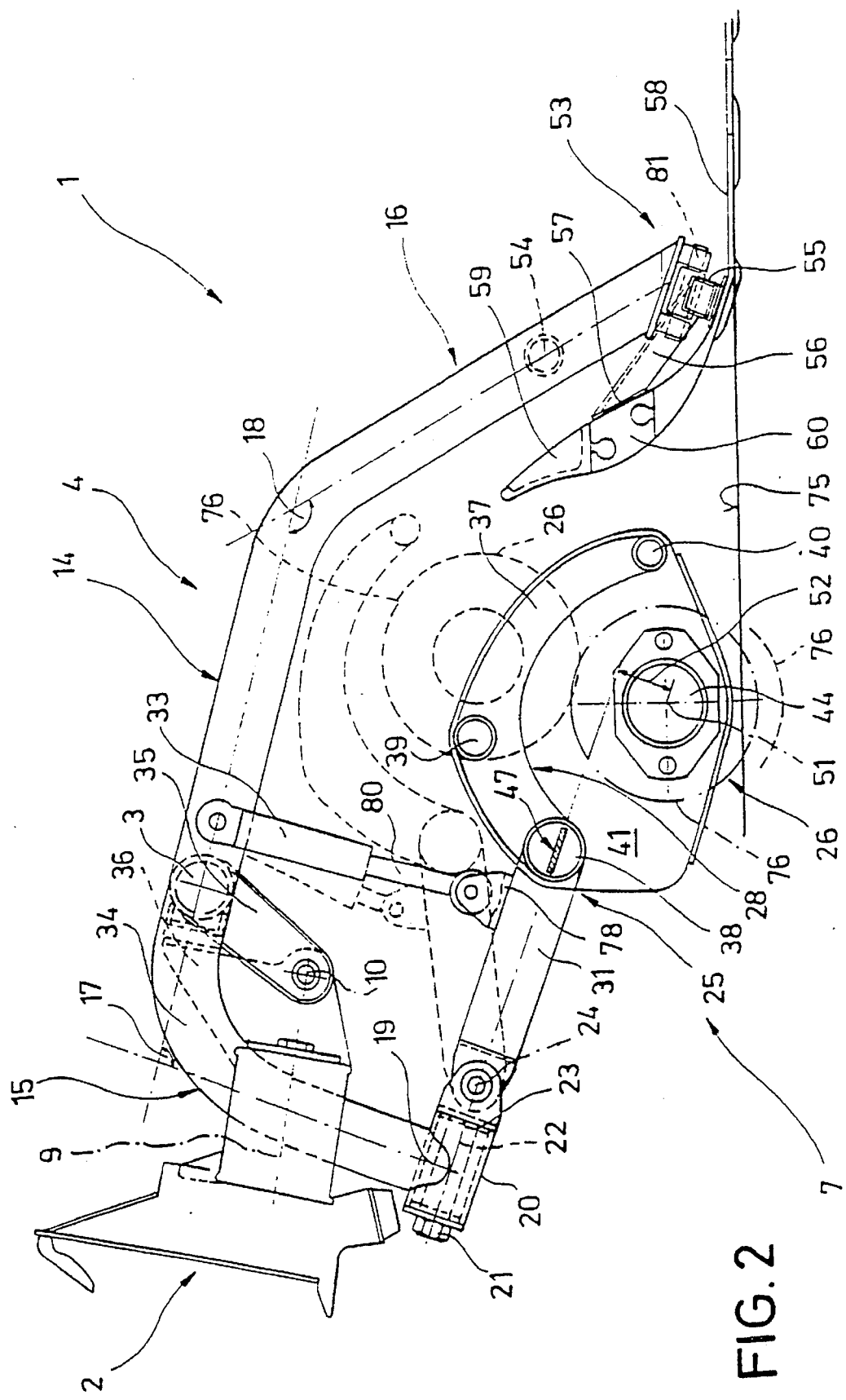
FIG. 2 shows a section along the line II—II of FIG. 1.

FIG. 2 shows the snow grooming device 1 along a section II—II of FIG. 1. Identical reference numerals have been used for identical parts of the snow grooming device, and only part of these reference numerals will be mentioned hereinbelow.

When seen in a side view, the longitudinal supporting member 4 is essentially U-shaped. A U-crosspiece 14 extends above the propeller shaft 26 such that it is inclined upwards in the direction of the coupling means 2. The transverse supporting member 3 is arranged at the end of said U-crosspiece 4 associated with the coupling means 2, said transverse supporting member 3 having essentially the same height as said U-crosspiece 14. In the direction of the coupling means 2, the U-crosspiece 14 is followed by a U-leg 15 which extends, in the straight portion thereof, approximately at right angles 17 to said U-crosspiece 14. Said U-leg 15 is provided with a connecting portion 34 which has a curvature corresponding to approximately ¼ of a circle and which serves to connect the said U-leg 15 to said crosspiece 14. The connecting portion 34 merges with said U-crosspiece 14 adjacent the transverse supporting member 3. The U-leg 15 has secured thereto the bearing sleeve 20 at the free end thereof. A bearing bolt 21 is mounted within said bearing sleeve such that it is adapted to be rotated about the longitudinal axis 22. At the rear end 23 of the bearing bolt 21, the longitudinal control arm 31 is mounted by means of an additional bearing bolt, said longitudinal control arm 31 being mounted such that it is adapted to be pivoted about the essentially horizontal transverse axis 24. The end of the longitudinal control arm 31 associated with the bearing sleeve 20, cf. also FIG. 1, is mounted between two bearing brackets protruding from said bearing sleeve.

The end of the longitudinal control arm 31 located opposite the bearing sleeve 20 is secured to the baffle casing 28. Said baffle casing 28 consists of an approximately semicircular hollow section 37 shielding the propeller shaft 26 towards the top. The hollow section 37 has arranged therein three reinforcement tubes 38, 39 and 40 extending parallel to the axis of rotation 51 of the propeller shaft 26. The reinforcement tube 38 having the largest diameter is inserted in the front end of the baffle casing 37 and connected to the longitudinal control arm 31 by the additional reinforcement sheet 78. The resetting device 47 is arranged within the reinforcement tube 38. According to FIG. 1, the resetting device extends essentially parallel to the transverse direction 50 of the snow grooming device 1 in the longitudinal direction. According to FIG. 2, the resetting device 47 extends in the transverse direction thereof parallel to the longitudinal direction of the longitudinal control arm 31 and approximately centrally with respect thereto.

Directly adjacent to the baffle casing 28, a lower end of the adjusting means 33 is pivotably mounted on the reinforcement sheet 78. The opposite upper end is pivotably mounted on the side face of the U-crosspiece 14. A vertical adjustment of the snow propeller 7 is effected by varying the degree of extension of a piston 80 of said adjusting means 33. In FIG. 2, the propeller shaft 26 is shown in a position at which its circumferential line 76 is partly immersed in a piste surface 75. By actuating the adjusting means 33, the propeller shaft 26 can be vertically adjusted so that it will occupy the positions outlined by broken lines.

For improved adaptation to the configuration of the longitudinal supporting member 4, the section of the baffle casing 37 extending between the reinforcement tube 39 and the reinforcement tube 40, which is inserted at the rear end thereof, is slightly bent downwards in comparison with the section of said baffle casing extending between the reinforcement tubes 38 and 39. The inner side of the baffle casing 37 associated with the propeller shaft 26 has an essentially semicircular shape. The axis of rotation 51 of the propeller shaft 26 extends at a distance 52 from the longitudinal control arm 31 below an axis defined by the extended central longitudinal axis of said longitudinal control arm 31.

The baffle casing 28 is covered at one lateral end thereof by an apron 41 and at the other lateral end thereof by an apron 42. The aprons are used for laterally holding the reinforcement tubes 38, 39 and 40 as well as for supporting the propeller shaft 26. They extend along the baffle casing 37 and merge positively therewith at the upper end thereof. Towards the bottom, the aprons cover most of the propeller shaft 26, the drive means 44 of the propeller shaft 26 being secured to the apron by means of two screws. The lower end of the apron extends from the reinforcement tube 40 at an oblique angle downwards up to a point below the axis of rotation 51 and from this point upwards approximately parallel to the longitudinal control arm 31. The front of the apron, which faces the longitudinal control arm 31, extends approximately vertically upwards, the contour of said apron corresponding to that of the baffle casing 37 from the reinforcement tube 38 onwards.

Towards the back, the U-crosspiece 14 is followed by the U-leg 16 which protrudes towards the back at an obtuse angle 18. The U-leg 16 has a length which exceeds that of the U-leg 15 and extends up to a point close to the piste surface 75. Adjacent the free end 53 thereof, a reinforcement transverse supporting member 54 is arranged, the height of said reinforcement transverse supporting member 54 being lower than that of the longitudinal supporting member 4.

The smoothing board strip 55 is mounted on the free end 53 of the U-leg 16 such that it is adapted to be pivoted about an axis of rotation 81 which extends parallel to the longitudinal axis 22 of the bearing sleeve 20. The smoothing board strip consists of a hollow section, which is secured to the smoothing blade 58 opposite to said U-leg 16. In the direction of the coupling means 2, the smoothing board carrier member 56 projects from the smoothing board strip 55 at an oblique angle upwards. The free end 57 of said smoothing board carrier member 56 is releasably secured to the carrier body 60. The cross-section of the carrier body 60 has approximately the shape of a parallelogram, the shorter sides of said parallelogram having provided therein dovetaillike grooves which are engaged by complementary projections of the smoothing blade 58 and the guard 59. The longer sides of the parallelogram of said carrier body 60 are essentially straight on the side facing the end 57 of the smoothing board carrier member 56 and, on the opposite side, they are convex in the direction of the propeller shaft 26. This convex curvature is continued by the lower surface of the smoothing blade 58 in the direction of the piste surface 75, whereas the side of the guard 59 facing the propeller shaft 26 is concave and merges positively with the carrier body 60.

A plurality of longitudinally extending, known projections is arranged below the smoothing blade 58. The smoothing board strip 55 is arranged above the foremost projection, said smoothing board strip 55 setting the front portion of the smoothing blade 58 at an acute angle relative to the piste surface 75. The smoothing blade portion following the smoothing board strip 55 rests on the piste surface 75 and penetrates into said piste surface with said projections.

Figure 3:
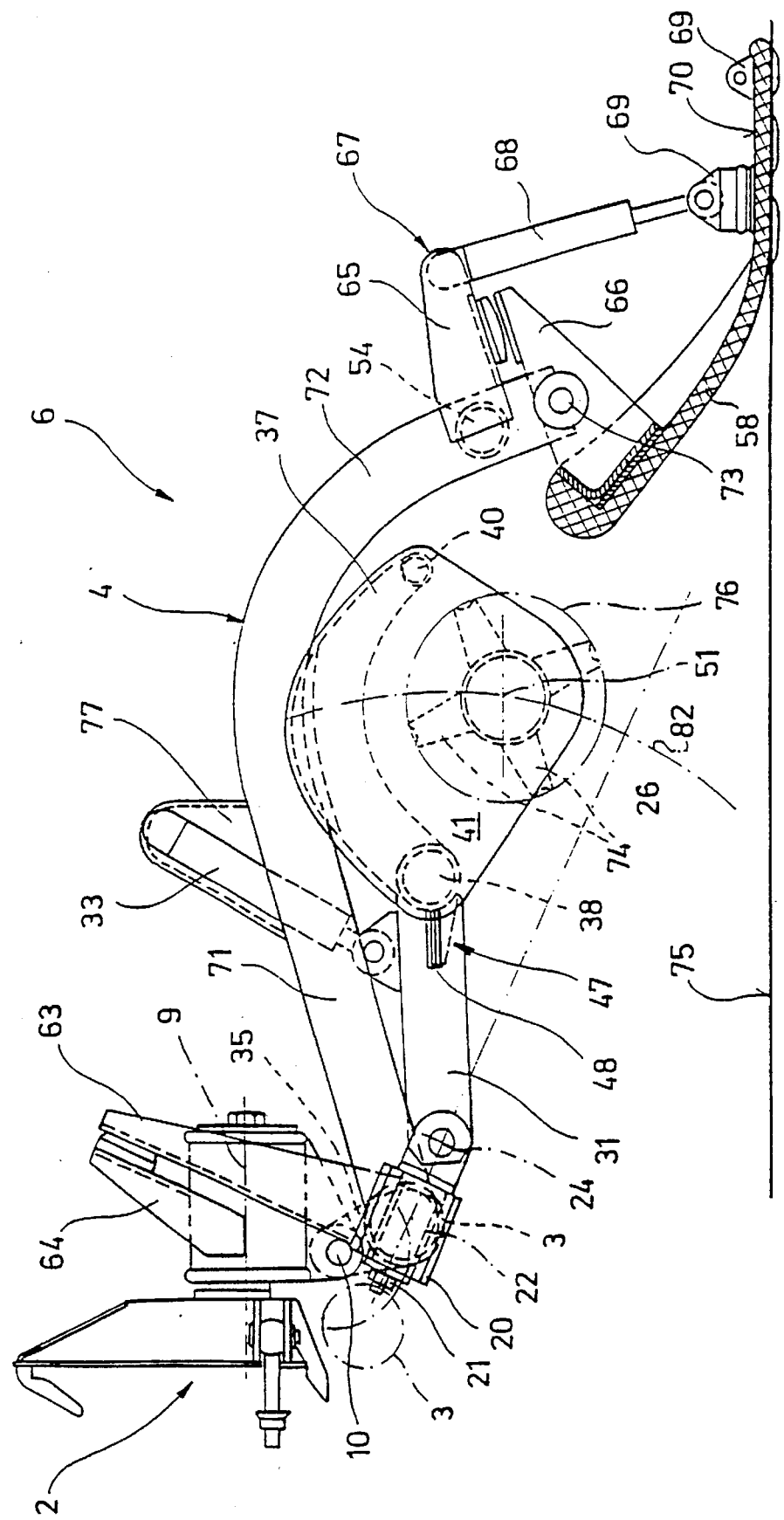
FIG. 3 shows an additional embodiment of the present invention in a representation corresponding to FIG. 2.

FIG. 3 shows an additional embodiment of the snow grooming device according to the present invention. Identical reference numerals have again been used for identical parts, and only part of these reference numerals will be dealt with hereinbelow.

The carrier frame 6 comprises longitudinal supporting members 4 and 5 and a transverse supporting member 3 as well as a reinforcement transverse supporting member 54. The longitudinal supporting members 4 are essentially L-shaped, the transverse supporting member 3 connecting the spaced longitudinal supporting members 4 at the free end of the longer L-leg 71. The shorter L-leg 72 is connected to said longer L-leg 71 via a curvature corresponding to approximately ¼ of a circle, the smoothing blade 58 being pivotably supported on the free end of said shorter L-leg 72.

The bearing sleeve 20, which is used for supporting the bearing bolt 21 such that it is adapted to be rotated about the longitudinal axis 22, is arranged at the side of the L-leg 71 when seen in the longitudinal direction of the transverse supporting member 3. Analogously with the representation according to FIG. 2, the longitudinal control arm 31 is supported on the end of the bearing bolt 21 such that it is adapted to be pivoted about the essentially horizontal transverse axis 24.

At the position shown in FIG. 3, the propeller shaft 26 has been raised from the piste surface 75 by the adjusting means 33. Said adjusting means 33 is arranged between the upper surface of the longitudinal control arm 31 and a holding bracket 77 projecting upwards from the L-leg 71. The adjusting means 33 is pivotably mounted at the respective ends thereof.

At the side of the longitudinal control arm 31, the resetting device 47 is arranged, said resetting device 47 projecting radially from the hollow tube 38. The ends of the flat connector 48 are held from above and from below by flanges projecting from said hollow tube 38. The length of said flanges in the direction of the longitudinal control arm 31 corresponds to the width of the flat connector 48.

According to FIG. 3, the baffle casing 37 is reinforced by two reinforcement tubes 38 and 40 at the ends thereof. In contrast to the curvature of the baffle casing 37 shown in FIG. 2, the curvature of the upper surface of the baffle casing 37 is uniform and corresponds to approximately ¼ of a circle. Below the baffle casing 37, the propeller shaft 26 provided with a plurality of radially projecting cutting blades 74 is rotatably mounted in the lateral apron 41. With the aid of the adjusting means 33, the axis of rotation 51 of the propeller shaft 26 is adapted to be moved along the circular line 82 for vertically adjusting the propeller shaft.

The essentially horizontal transverse axis 10, which is used for rotatably mounting the carrier frame 6, is arranged above the transverse supporting member 3, said transverse supporting member 3 being mounted on said transverse axis 10 via bearing brackets 35 projecting in the direction of the coupling means 2 forwards and upwards at an oblique angle. A stop lever 63 protrudes from said transverse supporting member 3 approximately at right angles to the longitudinal axis 22 of the bearing sleeve 20. The cross-section of said stop lever 63 corresponds approximately to the shape of a right-angled triangle. At the upper end of the longer leg of said right-angled triangle, the stop lever 63 is in contact with an abutting arm 64 protruding from the coupling means 2. This abutting arm 64 is inclined towards the back at an acute angle relative to the vertical; a buffer is arranged between said abutting arm and said stop lever.

At the free end of the L-leg 72, the smoothing blade 58 is mounted such that it is adapted to be pivoted about an essentially horizontal transverse shaft 73. The smoothing blade 58 has a semicircular front end, a step being formed between said front end and the smoothing blade 58 which extends towards the back; an abutting lever 66 is arranged in said step. Said abutting lever 66 is releasably connected to the smoothing blade 58 via the side facing said smoothing blade 58 and it is, approximately at the centre thereof, pivotably mounted on said transverse shaft 73. At its end located opposite the smoothing blade 58, the abutting lever 66 abuts on a stop arm 65 protruding from the reinforcement transverse supporting member 54 backwards and upwards. A buffer on which the free end of the abutting lever 66 can abut is arranged approximately at the centre of the longitudinal dimension of the stop arm 65. An adjustment means 68 is pivotably mounted on the free end 67 of said stop arm 65. The lower end of said adjustment means 68 is connected to a bearing bracket 69 protruding from the upper surface 70 of the smoothing blade 58. The portion of the smoothing blade 58 below the adjustment means 68 and the subsequent end of the smoothing blade 58 rest on the piste surface 75. The portion of the smoothing blade 58 preceding the adjustment means 68 is held at an acute angle of inclination relative to the piste surface 75 by means of the abutting lever 66 and the stop arm 65.

I claim:

1. A snow grooming device adapted to be attached to a vehicle with the aid of a coupling means, comprising a carrier frame, which consists of at least one transverse supporting member and two longitudinal supporting members each having a front end on which a vertically adjustable snow propeller is mounted and a smoothing board is mounted on the longitudinal support, said carrier frame being mounted on said coupling means such that said carrier front is adapted to be pivoted about an essentially horizontal longitudinal axis and an essentially horizontal transverse axis, such that the snow propeller is dragged by the front ends of the longitudinal supporting members and is pivotably mounted thereon and that the transverse supporting member, which is used for supporting the carrier frame, is pivotably supported at the coupling means.

2. A snow grooming device according to claim 1, wherein the transverse supporting member extends between the longitudinal supporting members and is, essentially at the centre thereof, pivotably mounted on said coupling means.

3. A snow grooming device according to claim 1, wherein the longitudinal supporting members are formed in a vertical plane and that they are essentially U-shaped, each of said longitudinal supporting members comprising a U-crosspiece and a front and a rear U-leg.

4. A snow grooming device according to claim 3, wherein the front U-leg associated with the snow propeller defines essentially a right angle with the U-crosspiece, and that the rear U-leg associated with the smoothing board defines an obtuse angle with said U-crosspiece.

5. A snow grooming device according to claim 4, such that for pivotably mounting the snow propeller, a bearing sleeve is arranged on the free end of the front U-leg, said bearing sleeve being used for receiving therein a bearing bolt which is adapted to be rotated about an essentially horizontal longitudinal axis and at the rear end of which the snow propeller is mounted such that it is adapted to be pivoted about an essentially horizontal transverse axis.

6. A snow grooming device according to claim 4, wherein the snow propeller comprises a propeller frame and at least one propeller shaft rotatably mounted on said propeller frame, said propeller frame being articulated on the front U-legs.

7. A snow grooming device according to claim 6, wherein said propeller frame comprises an essentially semicircular baffle casing at the lateral ends of which the propeller shaft is rotatably supported, and at least two longitudinal control arms arranged between the U-leg ends and said baffle casing.

8. A snow grooming device according to claim 7, wherein at least one adjusting means for vertically adjusting the snow propeller is arranged between the longitudinal control arm and the U-crosspiece.

9. A snow grooming device according to claim 3, wherein the front U-leg is connected to the U-crosspiece via a connecting portion bent outward at an acute angle measured from the longitudinal direction of the front U-leg.

10. A snow grooming device according to claim 9, wherein the transverse supporting member is arranged adjacent to the connecting portions of the front U-legs between the U-crosspieces and is supported on the coupling means such that it is adapted to be pivoted about the essentially horizontal transverse axis.

11. A snow grooming device according to claim 10, wherein the transverse supporting member is mounted on the coupling means via two bearing brackets extending approximately in the direction of the free end of the front U-legs.

12. A snow grooming device according to claim 11, wherein the coupling means has arranged thereon a stop means for the transverse supporting member.

13. A snow grooming device according to claim 7, wherein the baffle casing of the propeller shaft consists of a hollow section with reinforcement tubes extending within said hollow section essentially parallel to the propeller shaft, said baffle casing being covered at the sides by aprons extending essentially at right angles to said propeller shaft.

14. A snow grooming device according to claim 6, wherein the snow propeller consists of two propeller shafts with adequate propeller frames, the longitudinal control arms of each propeller frame being arranged essentially centrally on the respective propeller frame when seen in the transverse direction.

15. A snow grooming device according to claim 14, wherein each propeller shaft has associated therewith a drive means.

16. A snow grooming device according to claim 14, wherein the drive means are arranged on outer, lateral ends of the propeller shafts.

17. A snow grooming device according to claims 14 or 15, wherein a resetting device is arranged between said propeller frames.

18. A snow grooming device according to claim 17, wherein the resetting device is arranged between the neighboring ends of the propeller frames.

19. A snow grooming device according to claim 18, wherein the resetting device is an elastic flat connector which extends between two reinforcement tubes of the baffle casing in the longitudinal direction and essentially parallel to the horizontal longitudinal axis of the longitudinal control arm in its transverse direction.

20. A snow grooming device according to claims 6 or 14, wherein an axis of rotation of the propeller shaft is arranged below the longitudinal control arm at a distance therefrom.

21. A snow grooming device according to claim 3, wherein a reinforcement member is arranged adjacent to the free ends of the rear U-legs, said reinforcement member extending essentially parallel to the transverse supporting member.

22. A snow grooming device according to claim 21, wherein transversely extending smoothing board strips are pivotably supported on the free end of the rear U-leg.

23. A snow grooming device according to claim 22, wherein at least one smoothing board carrier member protrudes towards the front from each of said smoothing board strips, the free end of said smoothing board carrier member being releasably secured to the smoothing board.

24. A snow grooming device according to claim 23, wherein the smoothing board consists of a smoothing blade, a guard and a carrier body, said smoothing board carrier members being releasably secured to the carrier body and the guard protruding from said carrier body essentially upwards, whereas the smoothing blade protrudes therefrom essentially downwards.

25. A snow grooming device according to claim 24, wherein the smoothing blade and the guard are releasably secured to the carrier body.

26. A snow grooming device according to claims 14 or 25, wherein complementary to the snow propeller having two propeller shafts, at least the guard is divided in the transverse direction.

27. A snow grooming device according to claims 1 or 14, wherein the snow grooming device is constructed symmetrically with respect to the center line extending in the longitudinal direction.

28. A snow grooming device according to claim 11, wherein the transverse supporting member extends essentially between the front ends of the longitudinal supporting members and is pivotably mounted on the horizontal transverse axis via bearing brackets protruding in the direction of the coupling means.

29. A snow grooming device according to claim 28, wherein a stop lever protrudes from said transverse supporting member essentially upwards, said stop lever being adapted to be brought into abutting contact with an abutting arm arranged at the side of the coupling means.

30. A snow grooming device according to claim 17, wherein the resetting means is constructed as an elastic flat connector which extends laterally with respect to a reinforcement tube of said propeller frames and which is connected to said propeller frames.

31. A snow grooming device according to claim 24, wherein a stop arm protrudes backwards from the reinforcement transverse supporting member so that an abutting lever protruding from the smoothing board can abut thereon.

32. A snow grooming device according to claim 31, wherein an adjustment means is arranged between the free end of the stop arm and the smoothing board.

33. A snow grooming device according to claim 32, wherein at least one bearing bracket is formed on the upper surface of the smoothing board for releasably fastening the adjustment means.

34. A snow grooming device according to claim 26, wherein the snow grooming device is constructed symmetrically with respect to the center line extending in the longitudinal direction.

* * * * *

UNITED STATES PATENT AND TRADEMARK OFFICE
CERTIFICATE OF CORRECTION

PATENT NO. : 5,659,984
DATED : August 26, 1997
INVENTOR(S) : Walter Haug

It is certified that error appears in the above-indentified patent and that said Letters Patent is hereby corrected as shown below:

On the title page, item [73] Assignee: should be Kässbohrer

Geländefahrzeug GmbH, Germany

Signed and Sealed this

Eighteenth Day of November 1997

*Attest:*

BRUCE LEHMAN

*Attesting Officer*         *Commissioner of Patents and Trademarks*